United States Patent [19]

Shimizu

[11] Patent Number: 4,506,544

[45] Date of Patent: Mar. 26, 1985

[54] LEAKAGE DETECTOR OF ENDOSCOPES

[75] Inventor: Yoshihito Shimizu, Hachioji, Japan

[73] Assignee: Olympus Optical Co., Ltd., Japan

[21] Appl. No.: 477,409

[22] Filed: Mar. 21, 1983

[30] Foreign Application Priority Data

Mar. 19, 1982 [JP] Japan .................. 57-44273

[51] Int. Cl.³ ............................................ G01M 3/08
[52] U.S. Cl. ............................................ 73/45.5
[58] Field of Search ............................ 73/45.5, 40

[56] References Cited

U.S. PATENT DOCUMENTS 4,216,767 8/1980 Aoshiro.

FOREIGN PATENT DOCUMENTS 1228826 11/1964 Fed. Rep. of Germany ....... 73/45.5

Primary Examiner—S. Clement Swisher
Assistant Examiner—Joseph W. Roskos
Attorney, Agent, or Firm—Ostrolenk, Faber, Gerb & Soffen

[57] ABSTRACT

A leakage detector of endoscopes inspects cracks and pinholes within an endoscope of the perfect watertight structure by detecting leaked air therefrom while applying compressed air in the endoscope and, when no defect such as cracks and pinholes exists, controls by means of a relief valve so that the rise of air pressure within the endoscope assumes a given value.

8 Claims, 4 Drawing Figures

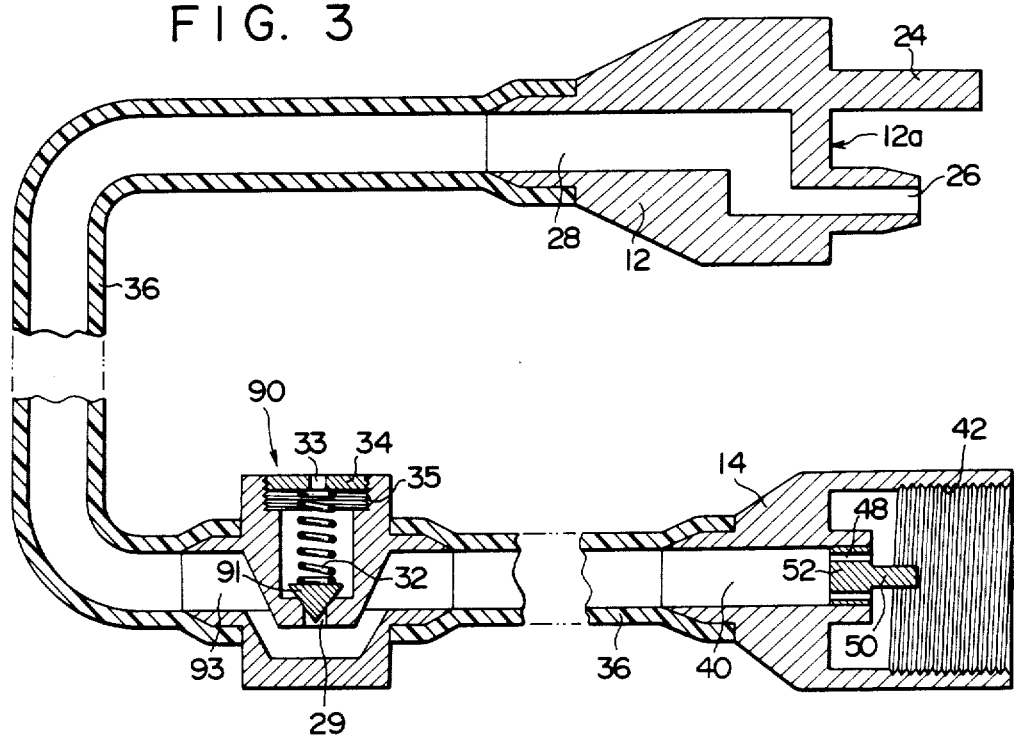
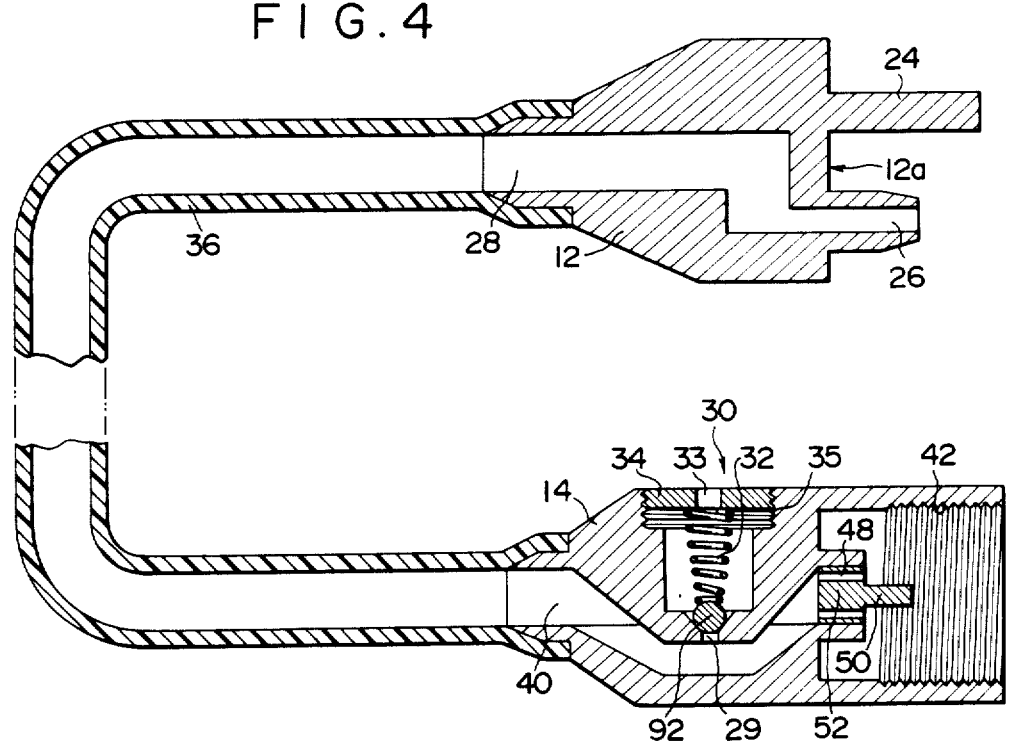

LEAKAGE DETECTOR OF ENDOSCOPES

BACKGROUND OF THE INVENTION

The present invention relates to a leakage detector for endoscopes, and more particularly, to a leakage detector for endoscopes of the perfect watertight type.

For reasons of sanitation, endoscopes are always washed and sterilized after use. Considering the convenience of washing and the like, there are provided endoscopes which have an entirely watertight structure including operating devices thereof so that it is possible easily to wash and sterilize the whole body by immersing it in a washing liquid and an antiseptic solution. However, when there are defects in the watertight structure of operating devices or pinholes and cracks in a sheath of the endoscope's flexible tube washing liquid can leak into the inside of the endoscope. This is highly undesirable since corrosion is caused inside of the endoscope and the washing liquid may leak into the bundle of optical fibers in the endoscope, resulting in hindrance to transmission of light. In addition, it is possible that patients will be harmed if washing liquid which is leaked into the inside of the endoscope leaks out of the endoscope while in use. To prevent these problems, Japanese Published Unexamined Utility Model Application No. Sho 53-114891 discloses a method wherein the internal pressure of the endoscope is raised above the external pressure outside the endoscope by providing an opening for applying compressed air into the endoscope. As a result, the leakage of a liquid into the endoscope when immersed in a washing liquid is prevented. According to this method, it is advantageously possible to easily find out a location where air comes out in the form of bubbles from pinholes, if any.

However, it is necessary to properly choose a value of pressure to be used when compressed air is applied, otherwise there would be a likelihood that the endoscope itself may be damaged by the pressure. If the pressure is controlled using a pump, the apparatus becomes disadvantageously complex.

In addition, it is extremely inconvenient that in order to apply compressed air into the endoscope a pump for exclusive use is always provided by the endoscope.

SUMMARY OF THE INVENTION

In view of the foregoing, it is an object of the invention to provide a leakage detector for endoscopes which detector is provided with a device of a simple structure for controlling air pressure to be applied into an endoscope of the perfect watertight type into which air is admitted to perform a leakage test.

According to the invention, it is possible to safely and securely perform a leakage test of endoscopes of the perfect watertight type which have a pressure inlet for a leakage detection without damaging the endoscope due to an application of overpressure thereto. In addition, since a pressure regulating screw is used for a retainer of a spring which restrains a relief valve, it is possible to properly adjust an applying pressure depending upon different types of endoscopes, thus enabling the leakage detector to be used with various types of endoscopes. By the provision of an adapter which is connectable to different kinds of compressed air sources in the leakage detector, it is not necessary to limit compressed air sources and it is advantageously possible to increase its universality.

BRIEF DESCRIPTION OF THE DRAWINGS

FIG. 3 is a section view of a leakage detector illustrating another embodiment of the invention; and FIG. 4 is a section view of a leakage detector illustrating a further embodiment of the invention.

DETAILED DESCRIPTION OF PREFERRED EMBODIMENTS

Figure 1:
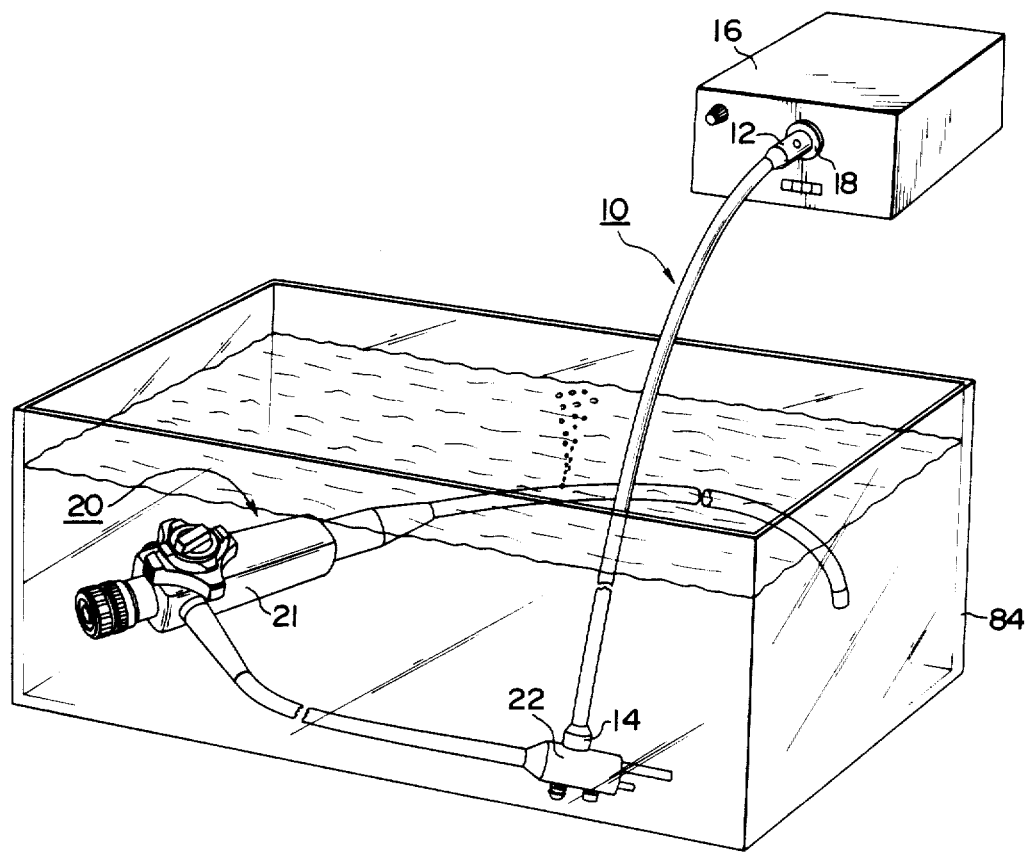
FIG. 1 is a perspective view illustrating an example of aspects in use of a leakage detector according to the invention.

Referring now to FIG. 1, a leakage detector 10 according to the invention is formed with a connector, one end of which has a first connector member 12 and the other end of which has a second connector member 14. The first connector member 12 is connected to a scope socket 18 of a light source apparatus 16 for an endoscope which includes an air supplying apparatus. The second connector member 14 is connected to a connector 22 of an endoscope 20 to be tested.

Figure 2:
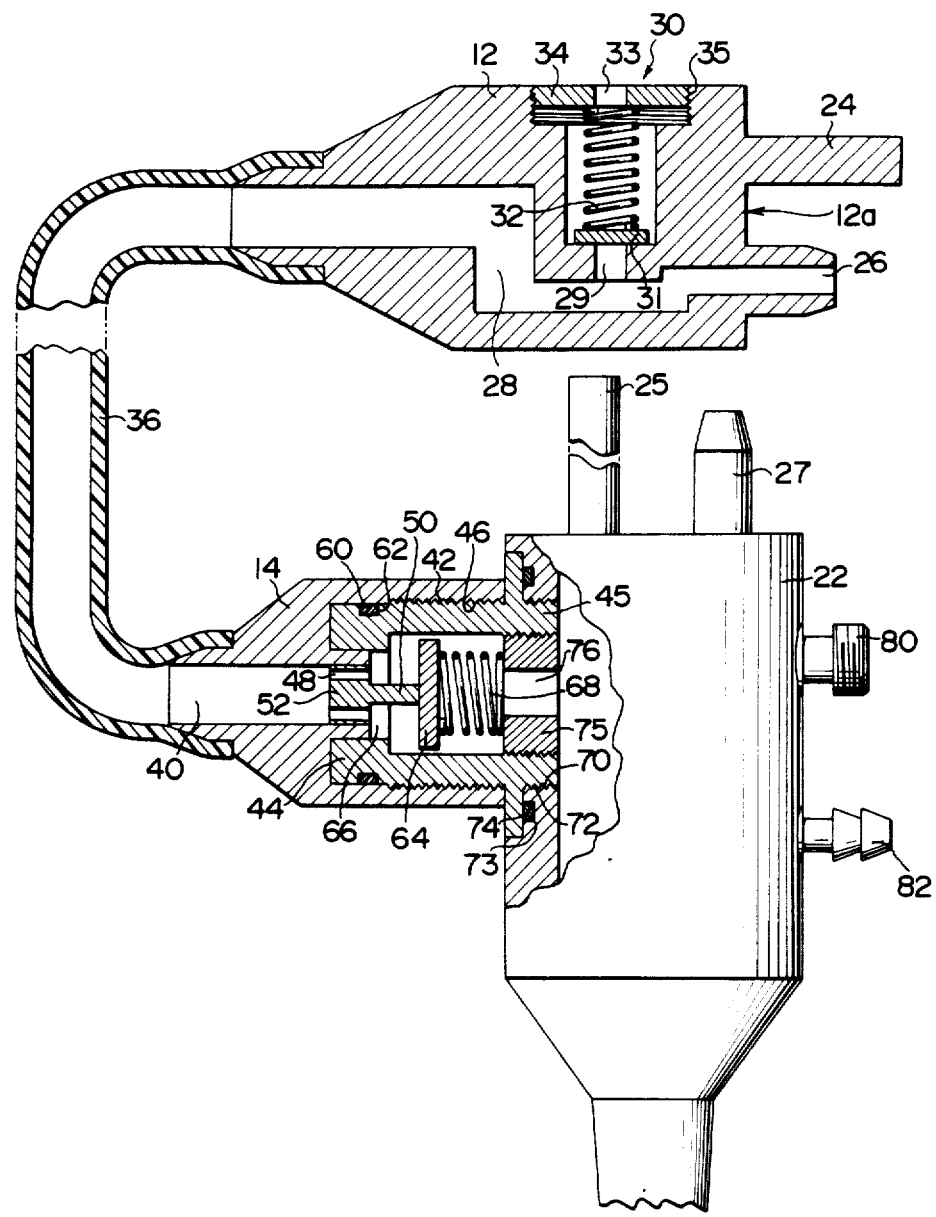
FIG. 2 is a section view of a leakage detector illustrating an embodiment of the invention.

Referring now to FIG. 2, which illustrates an internal structure of the leakage detector 10 of an embodiment of the invention which is connected as shown in FIG. 1, the first connector member 12 thereof has substantially the same shape and positional relationship as the connector 22 of the endoscope. One end surface 12a of the first connector member 12 is provided with a dummy inlet piece 24 whose external shape is equivalent to a light guide piece 25 of the endoscope and a port 26 for admitting compressed air which has the same shape as a piece 27 for admitting air of the endoscope. The dummy inlet piece 24 serves as a guide pin when the first connector member 12 is fixed to the light source apparatus 16. The port 26 through which compressed air is admitted from an air supplying apparatus (not shown) in the light source apparatus 16, communicates with a first passage 28 which leads compressed air.

The inside of the first connector member 12 is provided with a relief valve member 30 communicating with the first passage 28 for maintaining the pressure at the inlet of passage 28 constant. The relief valve member 30 is composed of a relief valve body 31 for closing a relief port 29 branching from the first passage 28, a coiled spring 32 which presses the valve body 31 against the rim of port 29 and a laminal spring retainer 34 having a hole 33. The spring retainer 34 is provided with male threads 35 on its periphery so as to adjust the force of spring 32 in accordance with a threaded depth of the retainer 34.

The first passage 28 is hermetically connected to one end of a tube 36 which forms a passage of admitting air and communicates with a second passage 40 which is provided in the second connector member 14 by hermetically connecting the other end of tube 36 to the second passage 40. The second connector member 14 is provided with female threads 42 on its end inside thereof so as to be threaded on male threads 46 provided on the outside periphery of a compressed air admitting portion 44 which is projected from the connector 22 of the endoscope. Additionally, the inside of the second connector member 14 is provided with a compressed air applying portion 52 which enters a central port 66 which will be described later and which is provided with a projection 50 having a plurality of communicating holes 48 on its circumference.

The compressed air admitting portion 44 of the endoscope has a inlet port 66 on its central axis and the inlet port 66 is closed by means of an inlet valve 64 which is urged toward port 66 by a coiled spring 68. A spring retainer 75, which supports the spring 68, is integrally threaded into the admitting portion 44 and is provided with a through-hole 76 communicating the inlet port 66 with the inside of the endoscope. A circumferential groove 62 is provided on the outside periphery of the admitting portion 44 and receives a packing 60 which maintains airtightness between portion 44 and connecting member 14. The admitting portion 44 is integrally attached to the connector 22 by a male thread 70 which is provided on the outside periphery of a fitting portion 45 and a female thread 72 which is provided on the inside periphery of through-hole of the connector 22. In order to keep airtightness of the attached portion between the connector 22 and the portion 44, a circumferential groove 73 is provided around the through-hole 76 of the connector 22 and a packing 74 is inserted in the groove 73.

In addition, an inlet piece 80 for admitting air and water and an outlet piece 82 for suction are provided on the side of the connector 22.

The embodiment of the leakage detector of the invention described above, is used to detect pinholes or the like by connecting the first connector member 12 to the light source apparatus 16 for endoscopes, connecting the second connector member 14 to the compressed air admitting portion 44 of connector 22 of the perfect watertight endoscope 20 and then immersing the endoscope 20 into a tank 84 holding water (or cleaning liquid, antiseptic solution). See FIG. 1.

In operation, when the first connector member 12 is connected to the scope socket 18 which forms an air supplying portion of the light source apparatus 16, compressed air to be supplied when the air admitting piece 27 of the connector 22 is connected is normally applied to the compressed air admitting port 26. The compressed air is the same as used when air and water are supplied while the endoscope is used. The compressed air applied from the light source apparatus 16 is led through the port 26 of the first connector member 12, the first passage 28 and the tube 36 to the second passage 40 within the second connector member 14. When the second connector member 14 is threaded into the air admitting portion 44 of the connector 22, the inlet valve 64 within the portion 44 is pushed in by means of the projection 50 within the second connector member 14 so that the inside of the portion 44 communicates with the second passage 40 through holes 48 of the air applying portion 52. As a result, the compressed air from the light source apparatus 16 is supplied through the second passage 40, the inside of the portion 44 and the through-hole 76 to the inside of the connector 22. Consequently, the compressed air from the light source apparatus 16 is applied to the inside of the endoscope 20 so that it is possible to detect locations at a glance where defects such as pinholes, if any, exist on the outside surface thereof since bubbles are produced from the defects.

The relief valve body 31 which maintains air pressure applied to the endoscope constant when there is no defect in the endoscope so that airtightness is maintained, is opened by being pushed since the spring 32 yields to the applied air pressure when it exceeds a given level. As a result, it is possible to maintain the applied pressure constant, to prevent the endoscope from being damaged and to always inspect with a constant applied pressure. In addition, the spring retainer 34 makes it possible to adjust the initial force of spring 32 depending upon the endoscope being tested.

During leakage detection, washing liquid enters the inside of the air admitting tube of the connector 22, the inlet piece 80 for air and water, and the outlet suction piece 82 of the perfect water-tight endoscope 20. However, since these parts form one tube communicating the inlet port with the outlet port of the tip end of the endoscope, washing liquid does not penetrate into the inside of the endoscope but it is rather preferred that washing liquid enters from the inlet port to the inside of the tube since the inside of the endoscope is washed simultaneously when washed as a whole.

No washing liquid penetrates into the light guide piece 25 of the connector 22 since it is applied a waterproofing.

A second embodiment of a leakage detector according to the invention will now be described by referring to FIG. 3. Like reference characters designate corresponding parts of the first embodiment and the description of the corresponding parts will be omitted.

In the second embodiment, a relief valve portion is not provided within the first connector member 12 but a relief valve portion 90 is provided in the middle of the 36, within which a conical-shaped relief valve 91 is provided. The relief valve portion 90 has a passage 93 in the side thereof, both ends of which are open and are connected to tubes 36. The other structures are similar to the first embodiment. A relief port 29 branching off from the passage 93 is closed by pressing a valve body 91 with a spring 32. The spring force is adjusted by an adjusting screw 35 of a spring retainer 34. According to this embodiment, advantages are that since a relief valve is not provided within connector members, the connector members may be of a reduced size and when the relief valve is located within water (when tube 36 is immersed as shown in FIG. 1) the action of the relief valve can be recognized as a result of the bubbles produced thereby. The action of the relief valve body 91, similar to that in the first embodiment, is to prevent a failure in endoscope 20 by opening the relief valve body 91 and ejecting air when air pressure within the endoscope 20 exceeds a given value.

Referring now to FIG. 4, a third embodiment of the invention will be described. As like reference characters designate corresponding parts of the first embodiment, the description of the corresponding part will be omitted. In this embodiment, a relief valve portion is provided within the second connector member 14 and a relief port 29 branches off from a second passage 40. The relief port 29 is closed by a ball-shaped relief valve body 92 which is pressed by a spring 32, similar to the first embodiment. The spring force is adjustable by means of an adjusting screw 35.

According to this embodiment, since the relief valve is provided within the second connector member 14, it is advantageously possible to definitely recognize the actions of relief valve body 92 through bubbles. The action of relief valve body 92 is in the same manner as that of the relief valve body 31 in the first embodiment.

The present invention is not limited to the foregoing embodiments. A compressed air source may be not only a light source apparatus for endoscopes but may be any apparatus which generates compressed air with a proper pressure. The first connector member may be of a structure in which compressed air is applicable from the compressed air source apparatus. By way of example, instead of providing the dummy inlet piece 24 in the foregoing embodiments a member having only a compressed air inlet port may be inserted into the scope socket of the light source apparatus. In addition, the first connector member may not be in the shape of a connector portion of the endoscope as well as in one body. One end of the first connector member may be an adapter which is connectable to a compressed air source to be used and the other end thereof may be a connector member in integral with the passage tube, thus enabling the first connector member to be connected through the adapter to the compressed air source. As a consequence, it is possible to apply the same leakage detector to different kinds of light sources and compressed air sources by exchanging adapters.

What is claimed is:

1. A leakage detector for endoscopes, comprising:
   a first connector member to be connected to a compressed air source;
   a second connector member to be connected to a compressed air inlet portion of an endoscope of the perfect watertight structure for feeding compressed air to the inside of said endoscope;
   a communicating tube for connecting said first and second connector members; and
   a pressure regulator which is formed in at least one of said first and second connector members and said communicating tube for regulating the pressure of compressed air in said endoscope when said leakage detector is connected between a source of compressed air and an endoscope of the perfect watertight structure.

2. A leakage detector for endoscopes according to claim 1, wherein said pressure regulator includes a pressure regulating screw in combination with a spring valve for adjusting the pressure in said communicating tube.

3. A leakage detector for endoscopes comprising:
   a first connector member to be connected to a compressed air source, said first connector member having a structure substantially identical in shape to a connector which connector is for feeding air and water into said endoscope and is to be connected to a scope socket of a light source apparatus which is provided with an air supplying apparatus;
   a second connector member to be connected to a compressed air inlet portion of an endoscope of the perfect watertight structure for feeding compressed air into the inside of said endoscope;
   a communicating tube for connecting said first and second connector members; and
   a pressure regulator which is formed in at least one of said first and second connector members and said communicating tube for regulating the pressure of compressed air in said endoscope when said leakage detector is connected between said air supplying apparatus and an endoscope of the perfect watertight structure.

4. A leakage detector for endoscopes, comprising:
   a first connector member to be connected to a compressed air source;
   a second connector member to be connected to a compressed air inlet portion of an endoscope of the perfect watertight structure for feeding compressed air to the inside of said endoscope;
   a communicating tube for connecting said first and second connector members; said second connector member having a compressed air applying portion which has a plurality of communicating holes and a projection which cooperate to allow the insides of said inlet portion and said communicating tube to communicate with each other through said communicating holes when said second connector member is connected to the inlet portion of said endoscope as a result of the fact that said projection pushes in an inlet valve for closing said inlet portion when said second connector is mounted on said compressed air inlet portion of said endoscope; and
   a pressure regulator which is formed in at least one of said first and second connector members and said communicating tube for regulating the pressure of compressed air in said endoscope when said leakage detector is connected between a source of compressed air and an endoscope of the perfect watertight structure.

5. A leakage detector for endoscope according to claim 1, 3 or 4, in which said pressure regulator is formed with a relief valve for automatically regulating the compressed air pressure within the endoscope at a given value.

6. A leakage detector for endoscopes according to claim 1, 3 or 4, wherein said pressure regulator is formed in said first connector member.

7. A leakage detector for endoscopes according to claim 1, 3 or 4, wherein said pressure regulator is formed in said communicating tube approximately halfway between said first and second connector members.

8. A leakage detector for endoscopes according to claim 1, 3 or 4, wherein said pressure regulator is formed in said second connector member.

* * * * *